United States Patent
Wang

(10) Patent No.: US 7,236,825 B2
(45) Date of Patent: Jun. 26, 2007

(54) CARDIAC ACTIVITY SENSING DURING PACING IN IMPLANTABLE DEVICES

(75) Inventor: Li Wang, White Bear Township, MN (US)

(73) Assignee: Medtronic, Inc., Minneapolis, MN (US)

( * ) Notice: Subject to any disclaimer, the term of this patent is extended or adjusted under 35 U.S.C. 154(b) by 574 days.

(21) Appl. No.: 10/836,359

(22) Filed: Apr. 30, 2004

(65) Prior Publication Data

US 2005/0245976 A1 Nov. 3, 2005

(51) Int. Cl.
*A61N 1/00* (2006.01)
*A61B 5/04* (2006.01)

(52) U.S. Cl. .................. 607/19; 607/9; 607/4; 607/2; 607/27; 607/115; 607/116; 600/372; 600/373; 600/374; 600/377; 600/381; 600/510

(58) Field of Classification Search .................. 607/9, 607/4, 2, 27, 115, 116, 122, 123; 600/372, 600/373, 374, 377, 381, 510
See application file for complete search history.

(56) References Cited

U.S. PATENT DOCUMENTS

| | | | |
|---|---|---|---|
| 4,379,459 A | 4/1983 | Stein | 128/419 PG |
| 4,428,378 A | 1/1984 | Anderson et al. | 128/419 PG |
| 4,485,813 A | 12/1984 | Anderson et al. | 128/675 |
| 4,702,253 A | 10/1987 | Nappholz et al. | 128/419 PG |
| 4,872,459 A | 10/1989 | Pless et al. | 128/419 PG |
| 4,991,583 A | 2/1991 | Silvian | 128/419 PG |
| 5,003,975 A | 4/1991 | Hafelfinger et al. | 128/419 PG |
| 5,117,824 A | 6/1992 | Keimel et al. | 128/419 D |
| 5,144,949 A | 9/1992 | Olson | |
| 5,193,536 A | 3/1993 | Mehra | 128/419 D |
| 5,209,229 A | 5/1993 | Gilli | 128/419 D |
| 5,222,493 A | 6/1993 | Sholder | 128/419 P |
| 5,324,310 A | 6/1994 | Greeninger et al. | 607/28 |
| 5,331,966 A * | 7/1994 | Bennett et al. | 600/508 |
| 5,417,718 A | 5/1995 | Kleks et al. | 607/28 |
| 5,709,709 A | 1/1998 | Kroll | |
| 5,725,561 A * | 3/1998 | Stroebel et al. | 607/9 |
| 5,792,192 A | 8/1998 | Lu | |
| 5,978,709 A | 11/1999 | Begemann et al. | 607/14 |
| 6,434,428 B1 | 8/2002 | Sloman et al. | 607/28 |
| 6,473,645 B1 * | 10/2002 | Levine | 607/9 |
| 6,477,417 B1 * | 11/2002 | Levine | 607/9 |
| 6,606,516 B2 * | 8/2003 | Levine | 607/9 |
| 6,699,200 B2 * | 3/2004 | Cao et al. | 600/508 |
| 6,937,901 B2 * | 8/2005 | Zhu et al. | 607/27 |

(Continued)

FOREIGN PATENT DOCUMENTS

EP 0313881 5/1989

*Primary Examiner*—Carl Layno
*Assistant Examiner*—Jon-Eric C. Morales
(74) *Attorney, Agent, or Firm*—Michael C. Soldner; Girma Wolde-Michael

(57) ABSTRACT

A method and device for sensing cardiac activity that includes a first plurality of electrodes forming a first electrode configuration to sense cardiac activity, a second plurality of electrodes forming a second electrode configuration to sense cardiac activity, and a third plurality of electrodes to deliver a stimulation pulse in response to the sensed cardiac activity. A microprocessor determines whether an escape interval associated with the delivered stimulation pulse is less than a rate limit interval, and a control circuit switches from the first plurality of electrodes to the second plurality of electrodes in response to the escape interval being less than the rate limit interval.

10 Claims, 6 Drawing Sheets

U.S. PATENT DOCUMENTS

| | | | |
|---|---|---|---|
| 6,975,904 B1 * | 12/2005 | Sloman | 607/28 |
| 7,006,869 B2 * | 2/2006 | Bradley | 607/28 |
| 7,065,398 B2 * | 6/2006 | Hettrick et al. | 600/515 |
| 7,065,405 B2 * | 6/2006 | Pastore et al. | 607/9 |
| 7,113,822 B1 * | 9/2006 | Kroll | 607/4 |
| 2001/0049543 A1 | 12/2001 | Kroll | 607/28 |
| 2002/0151934 A1 * | 10/2002 | Levine | 607/9 |
| 2002/0151935 A1 * | 10/2002 | Levine | 607/9 |
| 2003/0050671 A1 * | 3/2003 | Bradley | 607/27 |
| 2003/0083709 A1 * | 5/2003 | Zhu et al. | 607/27 |
| 2003/0105493 A1 * | 6/2003 | Salo | 607/9 |
| 2003/0187482 A1 * | 10/2003 | Pastore et al. | 607/9 |
| 2004/0098057 A1 * | 5/2004 | Pastore et al. | 607/11 |

* cited by examiner

CARDIAC ACTIVITY SENSING DURING PACING IN IMPLANTABLE DEVICES

FIELD OF THE INVENTION

The present invention relates generally to implantable cardiac stimulation devices and, in particular, to a method and system for sensing intrinsic cardiac activity during cardiac pacing.

BACKGROUND OF THE INVENTION

Implantable medical devices are available for treating cardiac arrhythmias by delivering electrical stimulation therapy for pacing, cardioverting or defibrillating the heart. Such a device, commonly known as an implantable cardioverter defibrillator or "ICD", senses a patient's heart rhythm and classifies the rhythm according to a number of rate zones in order to detect episodes of tachycardia or fibrillation or to detect a need for bradycardia pacing.

Upon detecting an abnormal rhythm, the ICD delivers an appropriate therapy. Cardiac pacing is delivered in response to a pathologically low rate or absence of sensed intrinsic depolarizations, referred to as P-waves in the atrium and R-waves in the ventricle. A pacing pulse must be of adequate energy to depolarize or "capture" the cardiac tissue. The lowest pacing pulse energy which captures the heart is referred to as the pacing or capture threshold.

In response to tachycardia detection, a number of tiered therapies may be delivered beginning with anti-tachycardia pacing therapies and escalating to more aggressive shock therapies until the tachycardia is terminated. Termination of a tachycardia is commonly referred to as "cardioversion." Ventricular fibrillation (VF) is a serious life-threatening condition and is normally treated by immediately delivering high-energy shock therapy. Termination of VF is normally referred to as "defibrillation."

The performance of an ICD depends on accurate sensing of intrinsic cardiac activity, such as P-waves and R-waves, in order to reliably detect arrhythmias. Typically, cardiac electrogram (EGM) sensing is performed in a bipolar manner between a "tip" electrode located at the distal end of a cardiac lead and a "ring" electrode spaced proximally from the tip electrode, or in a unipolar manner between either a tip or ring electrode and the ICD housing, referred to as a "can" or "case" electrode. Pacing is generally delivered using the tip electrode paired with either the ring electrode or ICD housing. Integrated bipolar leads are also known for use with ICDs in which a coil electrode is used, in place of the ring electrode, in combination with the tip electrode for bipolar pacing or sensing.

One limitation encountered when sensing cardiac signals using the same electrodes that are used for pacing is related to the afterpotential signal following delivery of a pacing pulse. Polarization at the electrode-tissue interface causes an afterpotential signal that can saturate sense amplifiers included in the cardiac pacing device and mask an evoked response signal. Sense amplifier circuitry may be temporarily disabled during and immediately following a pacing pulse to avoid saturation of sense amplifiers and the erroneous detection of the pacing pulse and post-pulse polarization artifacts. Reference is made, for example, to U.S. Pat. No. 4,379,459 issued to Stein. The post-pulse polarization artifact diminishes during the blanking interval, however, during this time the device is "blinded" to sensing cardiac signals, making detection of intrinsic or pacing-evoked depolarizations difficult.

In commercially available systems, capture is typically verified by sensing the evoked response following a pacing pulse. The challenges of sensing evoked cardiac signals are well-known in the art and have been addressed by a number of approaches in order to provide reliable capture management. Sensing the evoked response using an electrode pair that is different than the electrode pair used for delivering the pacing pulse can reduce or eliminate polarization artifact interference. Sensing a far-field signal related to an evoked response, as opposed to the near-field evoked response signal, or sensing a conducted depolarization away from the pacing site have also been proposed. See for example, U.S. Pat. No. 5,324,310 issued to Greeninger, U.S. Pat. No. 5,222,493 issued to Sholder, U.S. Pat. No. 5,331,966 issued to Bennett et al., U.S. Pat. No. 6,434,428 issued to Sloman, et al., and U.S. Pat. App. No. 20010049543, issued to Kroll. Depending on the associated lead system in use and the presence of conduction abnormalities, however, sensing far-field or conducted depolarizations using alternative sensing electrodes may not always be possible.

Regardless of the approach used for sensing pacing-evoked depolarizations, sense amplifier blanking during and after a pacing pulse blinds the device to sensing intrinsic depolarizations. At relatively high pacing rates, the duration of sense amplifier blanking during and after a pacing pulse may become substantial compared to the duration that the sense amplifier is enabled, significantly reducing the amount of time that the device is able to detect intrinsic activity. High rate intrinsic activity, such as during tachycardia or fibrillation, may consequently go undetected. Therefore, the maximum allowable pacing rate is typically limited in commercially available ICDs such that the detection of high rate arrhythmias is not impaired.

Rate-responsive pacemakers provide automatic adjustments to the pacing rate in response to a sensed signal indicative of the metabolic need of the patient. Rate-response sensors known for use with implantable cardiac stimulation devices include, for example, piezoelectric activity sensors and thoracic impedance sensing for estimating minute volume. Reference is made to U.S. Pat. No. 4,485,813 issued to Anderson, et al., and U.S. Pat. No. 4,702,253 issued to Nappholz et al. As the pacing rate is increased in response to increased metabolic need, the time in which the device is able to sense intrinsic activity is reduced when the sense amplifier blanking interval is fixed. Therefore, the device may limit the maximum rate-responsive pacing rate in order to preclude impaired sensing of intrinsic activity and arrhythmia detection. For example, the maximum upper pacing rate may correspond to a pacing escape interval equal to twice the sense amplifier blanking period, such that sensing is disabled no more than 50% of the time. Pacing at rates within tachycardia or fibrillation detection zones is typically avoided.

In some situations, however, this pacing rate constraint may prevent the physiological needs of the patient from being met, particularly in young, active patients. Relatively high pacing rates may be required to meet the metabolic needs of the patient, but higher rate pacing may be unavailable because of the pacing rate limitations imposed in order to prevent undersensing of high-rate intrinsic cardiac activity. Thus, it is desirable to provide rate-responsive pacing in ICDs without over-restricting the maximum pacing rate limit while still providing reliable detection of arrhythmias, and that reliably sense intrinsic cardiac activity during high rate cardiac stimulation.

BRIEF DESCRIPTION OF THE DRAWINGS

Aspects of the present invention will be readily appreciated as they become better understood by reference to the following detailed description when considered in connection with the accompanying drawings, wherein.

DETAILED DESCRIPTION OF THE INVENTION

Figure 1:
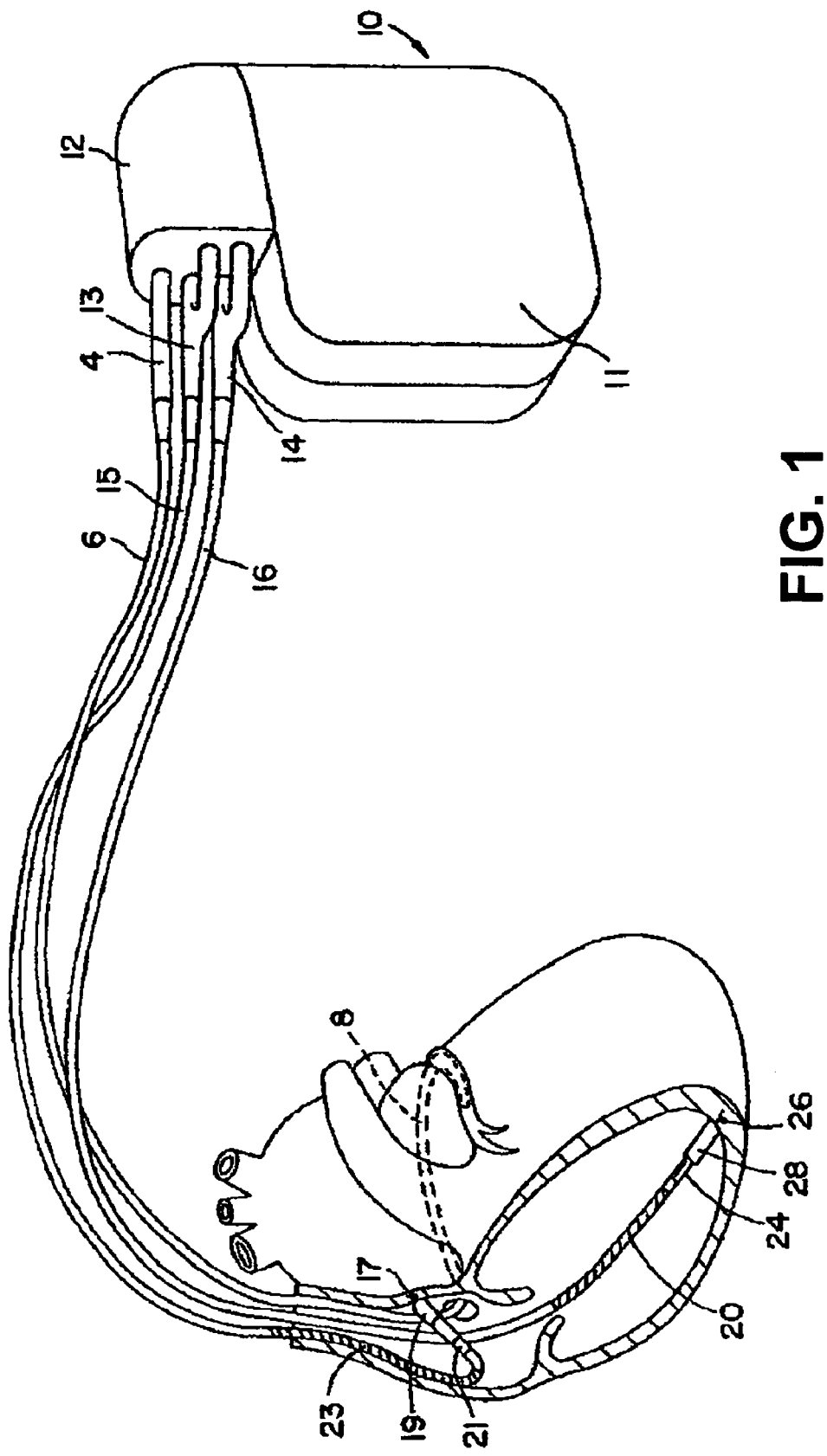
FIG. 1 is an illustration of an implantable cardiac stimulation device coupled to a patient's heart by way of three leads.

The present invention is directed toward providing an implantable cardiac stimulation system and method which allows cardiac stimulation pulses to be delivered at a relatively high rate without impairing the ability of the device to sense intrinsic cardiac activity and detect arrhythmias. As used herein, a "high stimulation rate" or "high pacing rate" generally refers to a rate that is greater than a maximum rate limit, which normally may not be exceeded and which may be set based on a blanking interval duration or an arrhythmia detection interval. The benefits of the present invention may be realized in an ICD having rate-responsive pacing capabilities. However, it is recognized that the present invention may be usefully practiced in any type of cardiac stimulation and monitoring system that, at times, employs relatively high rate cardiac stimulation, during which monitoring of intrinsic cardiac electrical activity is desired.

The present invention provides a cardiac stimulation system capable of reliably sensing intrinsic cardiac activity for the detection of arrhythmias during the delivery of cardiac stimulation at relatively high rates. The system includes an implantable cardiac stimulation device in which EGM sensing circuitry, pulse generating circuitry, and control circuitry are enclosed in a device housing. The system further includes one or more cardiac leads for positioning electrodes in operative relation to the heart for delivering cardiac stimulation pulses and sensing EGM signals. The system preferably includes at least one integrated bipolar cardiac lead or a tripolar or quadrapolar lead including a tip, ring, and one or more coil electrodes, for providing electrical stimulation therapies and for achieving sensing of intrinsic cardiac activity during stimulation at low, moderate or high rates.

The method for sensing intrinsic cardiac activity includes switching the sensing electrode configuration that is connected to device sensing circuitry from a default sensing configuration, for example a conventional tip-to-ring configuration (or tip-to-coil in an integrated bipolar lead), to a high pacing rate sensing configuration, which may be a coil-to-can, coil-to-coil or ring-to-coil configuration, when the stimulation rate exceeds a previously specified, upper stimulation rate. When the stimulation rate falls below the specified upper rate, the sensing configuration may be returned to the default sensing configuration.

In an alternative embodiment, an electrode configuration for sensing intrinsic cardiac activity during high rate stimulation may be connected to a dedicated sense amplifier that is enabled when the stimulation rate exceeds a specified upper rate. A default sense amplifier connected to a default sensing electrode configuration may be disabled when the dedicated, high pacing rate, sense amplifier is enabled, and the default sense amplifier may be re-enabled when intrinsic activity is sensed or when the stimulation rate falls below the specified upper stimulation rate.

FIG. 1 is an illustration of an implantable cardiac stimulation device 10 coupled to a patient's heart by way of three leads 6, 15, and 16. A connector block 12 receives the proximal end of a right ventricular lead 16, a right atrial lead 15 and a coronary sinus lead 6, used for positioning electrodes for sensing and stimulation in three or four heart chambers. In FIG. 1, the right ventricular lead 16 is positioned such that its distal end is in the right ventricle (RV) for sensing right ventricular cardiac signals and delivering electrical pulses in the right ventricle. For these purposes, right ventricular lead 16 is equipped with a ring electrode 24, a tip electrode 26, optionally mounted retractably within an electrode head 28, and RV coil electrode 20, each of which are connected to an insulated conductor contained within the body of lead 16. The proximal end of the insulated conductors are coupled to corresponding connectors carried by bifurcated connector 14 at the proximal end of lead 16 for providing electrical connection to the device 10.

The right atrial lead 15 is positioned such that its distal end is in the vicinity of the right atrium and the superior vena cava (SVC). Lead 15 is equipped with a ring electrode 21, a tip electrode 17 optionally mounted retractably within electrode head 19, and an SVC coil electrode 23 for sensing and stimulating in the right atrium. The ring electrode 21, the tip electrode 17 and the SVC coil electrode 23 are each connected to an insulated conductor with the body of the right atrial lead 15. Each insulated conductor is coupled at its proximal end to a connector carried by bifurcated connector 13. In alternative lead systems, an SVC coil electrode may be located on the right ventricular lead 16 rather than the right atrial lead 15 as shown in FIG. 1.

The coronary sinus lead 6 is advanced within the vasculature of the left side of the heart via the coronary sinus and great cardiac vein. The coronary sinus lead 6 is shown in the embodiment of FIG. 1 as having a coronary sinus (CS) coil electrode 8 that may be used in combination with either the RV coil electrode 20, the SVC coil electrode 23 and/or the device housing 11 for delivering electrical shocks for cardioversion and defibrillation therapies. In other embodiments, coronary sinus lead 6 may also be equipped with a distal tip electrode and one or more ring electrodes for stimulation and sensing functions in the left chambers of the heart. CS coil electrode 8 is coupled to an insulated conductor within the body of lead 6, which provides connection to the proximal connector 4.

The electrodes 17 and 21 or 24 and 26 may be used as bipolar pairs for sensing or stimulation, commonly referred to as a "tip-to-ring" configuration, or individually in a unipolar configuration with the device housing 11 serving as the indifferent electrode, commonly referred to as the "can" or "case" electrode. The device housing 11 may also serve as a subcutaneous defibrillation electrode in combination with one or more of the coil electrodes 8, 20 or 23 for defibrillation of the atria or ventricles. In accordance with the present invention, any of coil electrodes 8, 20 and 23 may also be made available for sensing EGM signals during high rate cardiac stimulation. Coil electrodes 8, 20, and 23 may be selected individually for sensing in combination with housing 11, or selected in pairs or in combination with ring electrode 21 or 24.

The depicted positions of the leads and electrodes shown in FIG. 1 in or about the right and left heart chambers are approximate and merely exemplary. Furthermore, it is recognized that alternative leads having other combinations of tip, ring, and coil electrodes provided for stimulating or sensing at particular sites in one or more heart chambers may be used in conjunction with the present invention. For example, instead of the tripolar leads shown, a quadrapolar lead having a tip electrode, ring electrode, and two coil electrodes may be used or an integrated bipolar lead having a tip electrode and one or more coil electrodes may be used. While a particular multi-chamber cardiac stimulation and lead system is illustrated in FIG. 1, methodologies included in the present invention may be applied in single chamber, dual chamber, or multi-chamber systems.

Figure 2:
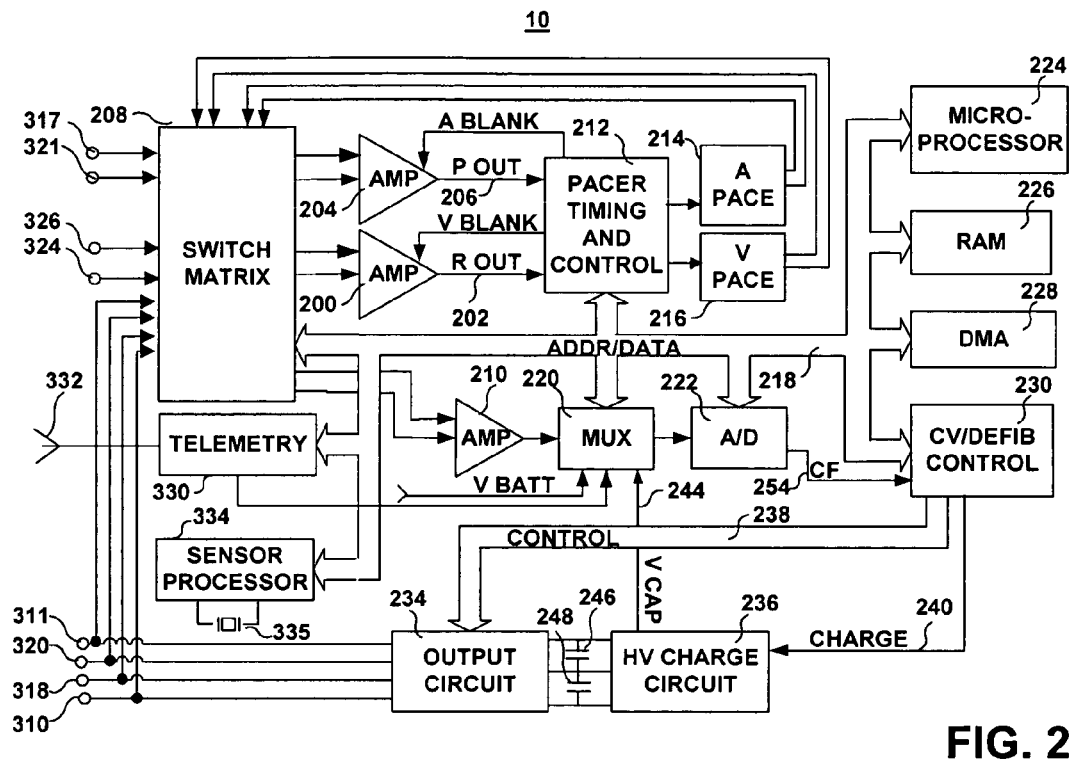
FIG. 2 is a functional block diagram of the cardiac stimulation device shown in FIG. 1 in which the present invention may be practiced.

FIG. 2 is a functional block diagram of the cardiac stimulation device shown in FIG. 1. This diagram should be taken as exemplary of the type of device with which the invention may be embodied and not as limiting, as it is believed that the invention may usefully be practiced in a wide variety of device implementations which are capable of sensing EGM signals and delivering cardiac stimulation therapies which at times employ delivery of stimulation pulses at a high rate. Stimulation therapies may include bradycardia pacing, rate-responsive pacing, cardiac resynchronization therapy, extra systolic stimulation, overdrive pacing for arrhythmia suppression or treatment of other cardiac-related conditions such as cardiac-related disordered breathing, rate stabilization pacing, or anti-tachycardia pacing, and may include higher voltage cardioversion and defibrillation therapies. The disclosed embodiment shown in FIG. 2 is a microprocessor-controlled device, but the methods of the present invention may also be practiced with devices employing dedicated digital circuitry for controlling some device functions.

With regard to the electrode system illustrated in FIG. 1, device 10 is provided with a number of connection terminals for achieving electrical connection to the cardiac leads 6, 15, and 16 and their respective electrodes. The connection terminal 311 provides electrical connection to the housing 11 for use as the indifferent electrode during unipolar stimulation or sensing. The connection terminals 320, 310, and 318 provide electrical connection to coil electrodes 20, 8 and 23 respectively. Each of these connection terminals 311, 320, 310, and 318 are coupled to the high voltage output circuit 234 to facilitate the delivery of high energy shocking pulses to the heart using one or more of the coil electrodes 8, 20, and 23 and optionally the housing 11.

In accordance with the present invention, connection terminals 311, 320, 310 and 318 are further connected to switch matrix 208 such that coil electrodes 8, 20, and 23 and housing 11 may be selected in desired combinations for connection to ventricular sense amplifier 200 or atrial sense amplifier 204 for use in sensing intrinsic cardiac signals.

The connection terminals 317 and 321 provide electrical connection to tip electrode 17 and the ring electrode 21 positioned in the right atrium. The connection terminals 317 and 321 are further coupled to an atrial sense amplifier 204 via switch matrix 208 for sensing atrial signals such as P-waves. The connection terminals 326 and 324 provide electrical connection to tip electrode 26 and the ring electrode 24 positioned in the right ventricle. The connection terminals 326 and 324 are further coupled to a ventricular sense amplifier 200 via switch matrix 208 for sensing ventricular signals.

The atrial sense amplifier 204 and the ventricular sense amplifier 200 preferably take the form of automatic gain controlled amplifiers with adjustable sensing thresholds. The general operation of the ventricular sense amplifier 200 and the atrial sense amplifier 204 may correspond to that disclosed in U.S. Pat. No. 5,117,824, by Keimel, et al., incorporated herein by reference in its entirety. Whenever a signal received by atrial sense amplifier 204 exceeds an atrial sensing threshold, a signal is generated on the P-out signal line 206. Whenever a signal received by the ventricular sense amplifier 200 exceeds a ventricular sensing threshold, a signal is generated on the R-out signal line 202. The sensing threshold may be automatically adjusted to a predetermined proportion of the amplitude of the detected P-wave or R-wave, and thereafter decays over a period of time to a lower, fixed sensing threshold level, which is typically programmable.

The A-PACE and V-PACE output circuits 214 and 216 are also coupled to terminals corresponding to desired stimulation electrodes via switch matrix 208. Atrial and ventricular sense amplifiers 214 and 216 are isolated from A-PACE and V-PACE output circuits 214 and 216 by appropriate isolation switches within switch matrix 208 and also by blanking circuitry operated by A-BLANK and V-BLANK signals at least during and optionally for a short time following delivery of a pacing pulse. The blanking interval applied may depend on the sensing electrode configuration selected.

Switch matrix 208 is used to select which of the available electrodes are coupled to sense amplifiers 200 and 204 for detecting cardiac activity and a wide band amplifier 210 for use in digital signal analysis. Selection of the electrodes is controlled by the microprocessor 224 via data/address bus 218. The selected electrode configuration may be varied as desired for the various sensing and stimulation functions of the device 10. In accordance with the present invention, during normal sensing and pacing operations, default sensing electrode configurations may be selected by switch matrix 208 for connection to sense amplifiers 200 and 204. For example, a default sensing electrode configuration may be a bipolar tip-to-ring sensing configuration for use during low or moderate stimulation rates or at times when no stimulation therapy is being delivered. When a relatively high stimulation rate is needed, however, different, high pacing rate sensing configurations are selected for connection to sense amplifiers 200 and 204. A high pacing rate configuration will generally include a coil electrode paired with the device housing, another coil electrode, or a ring electrode.

Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methods known in the art.

The telemetry circuit 330 receives downlink telemetry from and sends uplink telemetry to an external programmer, as is conventional in implantable anti-arrhythmia devices, by means of an antenna 332. Received telemetry is provided to microprocessor 224 via multiplexer 220. Data to be uplinked to the programmer and control signals for the telemetry circuit 330 are provided by microprocessor 224 via address/data bus 218. Numerous types of telemetry systems known for use in implantable devices may be used.

The remainder of circuitry illustrated in FIG. 2 is dedicated to the provision of cardiac pacing, cardioversion and defibrillation therapies and, for the purposes of the present invention, may correspond to circuitry known in the prior art. In the exemplary embodiment shown in FIG. 2, the pacer timing and control circuitry 212 includes programmable digital counters which control the basic time intervals associated with various single, dual or multi-chamber pacing modes, anti-tachycardia pacing therapies or other stimulation therapies delivered in the atria or ventricles. Pacer circuitry 212 also determines the amplitude of the cardiac pacing pulses under the control of microprocessor 224.

During pacing, escape interval counters within pacer timing and control circuitry 212 are reset upon sensing of R-waves or P-waves as indicated by signals on lines 202 and 206, respectively. In accordance with the selected mode of pacing, pacing pulses are generated by atrial pacer output circuit 214 and ventricular pacer output circuit 216. The pacer output circuits 214 and 216 are coupled to the desired electrodes for pacing via switch matrix 208. The escape interval counters are reset upon generation of pacing pulses, and thereby control the basic timing of cardiac pacing functions, including anti-tachycardia pacing.

The durations of the escape intervals are determined by microprocessor 224 via data/address bus 218. The value of the count present in the escape interval counters when reset by sensed R-waves or P-waves can be used to measure R-R intervals, P-P intervals, P-R intervals, and R-P intervals, which measures are stored in memory 226 and used to diagnose the occurrence of a variety of arrhythmias.

Microprocessor 224 operates as an interrupt driven device and is responsive to interrupts from pacer timing and control circuitry 212 corresponding to the occurrences of sensed P-waves and R-waves and corresponding to the generation of cardiac pacing pulses. Any necessary mathematical calculations to be performed by microprocessor 224 and any updating of the values or intervals controlled by pacer timing/control circuitry 212 take place following such interrupts. A portion of the random access memory 226 may be configured as a number of recirculating buffers capable of holding a series of measured intervals, which may be analyzed in response to a pace or sense interrupt by microprocessor 224 for diagnosing an arrhythmia. Any of the various arrhythmia detection methodologies known to the art may be employed.

In response to the detection of atrial or ventricular tachycardia, an anti-tachycardia pacing therapy may be delivered by loading a regimen from microcontroller 224 into the pacer timing and control circuitry 212 according to the type of tachycardia detected. In the event that higher voltage cardioversion or defibrillation shock pulses are required, microprocessor 224 activates the cardioversion and defibrillation control circuitry 230 to initiate charging of the high voltage capacitors 246 and 248 via charging circuit 236 under the control of high voltage charging control line 240. The voltage on the high voltage capacitors 246 and 248 is monitored via a voltage capacitor (VCAP) line 244, which is passed through the multiplexer 220. When the voltage reaches a predetermined value set by microprocessor 224, a logic signal is generated on the capacitor full (CF) line 254, terminating charging.

Delivery of cardioversion or defibrillation pulses is accomplished by output circuit 234, under control of control circuitry 230 via control bus 238. Output circuit 234 determines the shock pulse waveform, e.g. whether a monophasic, biphasic or multiphasic pulse is delivered, whether the housing 311 serves as cathode or anode, which electrodes are involved in delivery of the pulse, and the pulse shape and tilt. The timing of the delivery of the defibrillation or cardioversion pulse is controlled by pacer timing and control circuitry 212. Any known cardioversion or defibrillation pulse control circuitry may be usable in conjunction with the present invention.

In some embodiments, device 10 additionally includes a sensor 335 and sensor processing circuitry 334 used for detecting a physiological condition, such as metabolic demand. Sensor 335 may be located within the housing 11 of device 10 or may be located external to device 10, within the patient's body. Stimulation therapies may be adjusted in response to changes in a sensed physiological condition. For example, sensor 335 may be embodied as an activity sensor used for detecting the general activity of the patient. The pacing escape interval of the device may be altered in response to the detected activity level of the patient, as generally disclosed in U.S. Pat. No. 4,428,378, issued to Anderson, et al., incorporated herein by reference in its entirety. Other types of sensors and sensor processing circuitry are known for use in providing rate-responsive pacing. For example, impedance sensing may be used for determining a minute volume ventilation signal as generally disclosed in above-cited U.S. Pat. No. 4,702,253 issued to Nappholz or U.S. Pat. No. 5,709,709 issued to Kroll.

Figure 3:
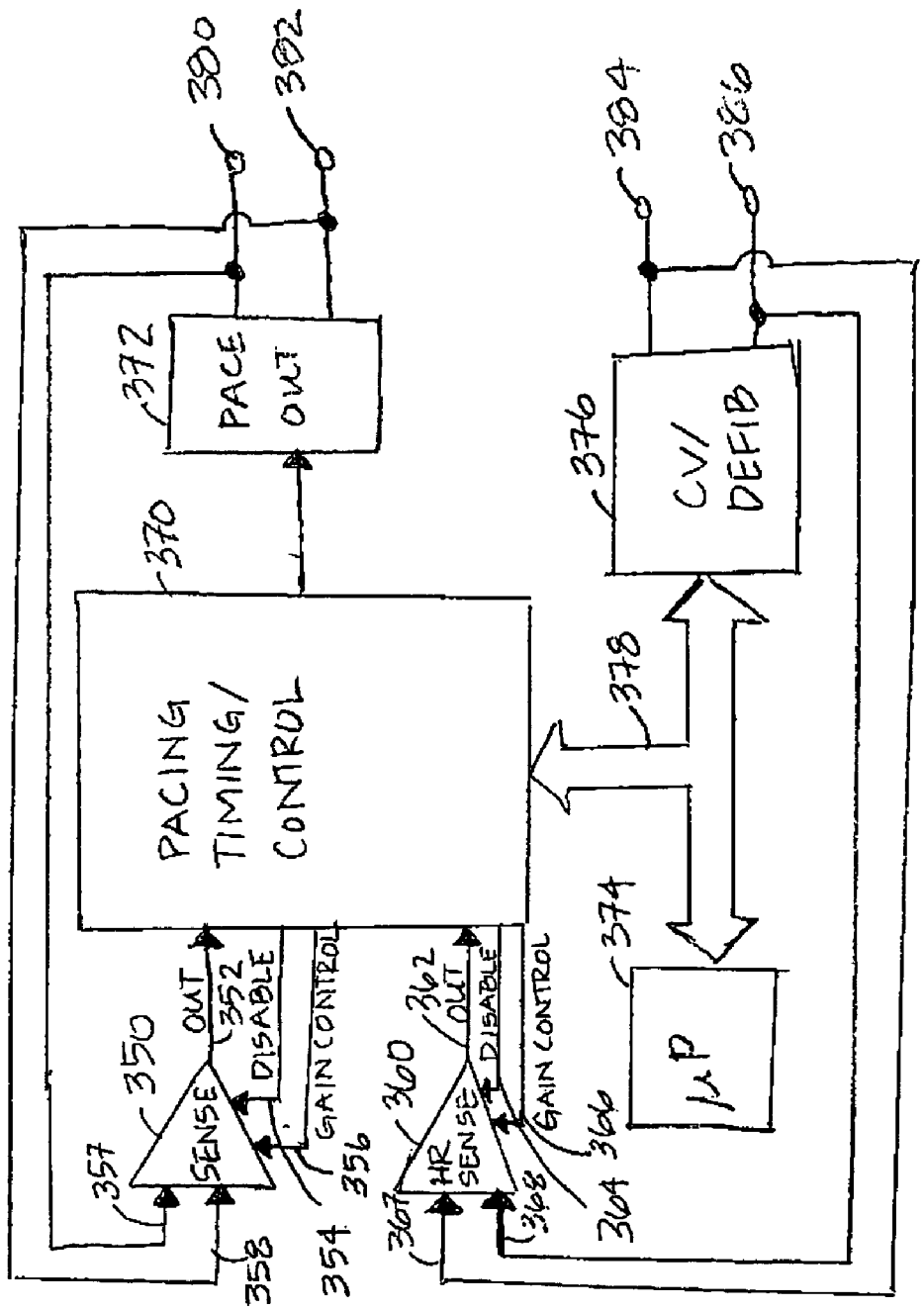
FIG. 3 is a functional block diagram of an alternative embodiment of a cardiac stimulation device in which the present invention may be practiced.

Alternative embodiments of the present invention may include a dedicated sense amplifier for sensing cardiac signals during high rate cardiac stimulation. Such embodiments may or may not include switching circuitry as described above for coupling electrodes selected for use in sensing during high rate stimulation. Default and high pacing rate sensing configurations may be coupled directly to corresponding, dedicated sense amplifiers. FIG. 3 is a functional block diagram of an alternative embodiment of a cardiac stimulation device in which the present invention may be employed that includes dedicated sensing circuitry for use during high rate stimulation. The device includes a microprocessor 374, pacing output circuitry 372, cardioversion/defibrillation output circuitry 376, and pacing timing and control circuitry 370 which are linked by control/data bus 378, and all of which may operate according generally to the description provided above in conjunction with FIG. 2, or as described previously in the above-cited U.S. Pat. No. 5,117,824 issued to Keimel, incorporated herein by reference in its entirety.

A default sense amplifier 350 and a dedicated high rate sense amplifier (HR SENSE) 360 are provided for sensing cardiac activity and generating an output signal on lines 352 or 362, respectively, to pacing timing and control circuitry 370. The default sense amplifier 350 is preferably enabled during low or moderate stimulation rates or when no stimulation is being delivered. The high rate sense amplifier 360 is preferably enabled during high rate stimulation.

Electrical signals from terminals 380 and 382 are provided as sensed signals to default sense amplifier 350 on input lines 357 and 358. Terminals 380 and 382 provide electrical connection to a default sensing electrode pair, e.g. a bipolar tip-to-ring pair, which may be the same electrode pair used for pacing and therefore be coupled to pacing output circuitry 372, as shown in FIG. 3. In response to the received sensed signals corresponding to detection of a cardiac signal, e.g. a P-wave or an R-wave, the default sense amplifier 350 provides a logic signal on output line 352 to pacing timing and control circuitry 370, which serves to reset the escape interval used to control the timing of stimulation pulse delivery.

If timing and control circuitry 370 does not receive a signal on output line 352 for a predetermined period of time corresponding to the escape interval set for controlling the timing of cardiac stimulation pulses, the timing and control circuitry 370 will trigger the generation of a pacing pulse by pacing output circuit 372. A disable signal on line 354 prevents sensing of the pacing pulse by default sense amplifier 350 while the pacing pulse is generated and for a predetermined time period thereafter.

If a determination is made that high rate stimulation is needed, default sense amplifier 350 is disabled, and high rate sense amplifier 360 is enabled. Pacing timing and control 370 controls the times at which default sense amplifier 350 and high rate sense amplifier 360 are enabled and disabled via signal lines 354 and 364, respectively. The gain of sense amplifiers 350 and 360 is also controlled by pacing timing and control 370 on signal lines 356 and 366, respectively.

High-rate sense amplifier 360 receives input on signal lines 367 and 368, which are coupled to terminals 384 and 386. Terminals 384 and 386 provide electrical connection to a high pacing rate sensing electrode configuration, which will generally include at least one coil electrode paired with another coil electrode, the device housing, or alternatively a ring electrode. High-rate sense amplifier 360 can be provided with filtering properties optimized to match the signal characteristics of the EGM signal received from the high pacing rate sensing electrode configuration. In the embodiment shown in FIG. 3, the electrodes used for sensing during high rate stimulation are also coupled to cardioversion/defibrillaion output circuitry 376 and used for cardioversion/defibrillation pulse delivery.

In a preferred embodiment, if an intrinsic cardiac signal is sensed by high rate sense amplifier 360, a logic signal is generated on output signal line 362, which causes pacing timing/control 370 to inhibit subsequent high rate stimulation pulses. High rate sense amplifier 360 is disabled, and default sense amplifier 350 is re-enabled such that intrinsic activity may be sensed, allowing any arrhythmia that may be present to be detected.

Figure 4:
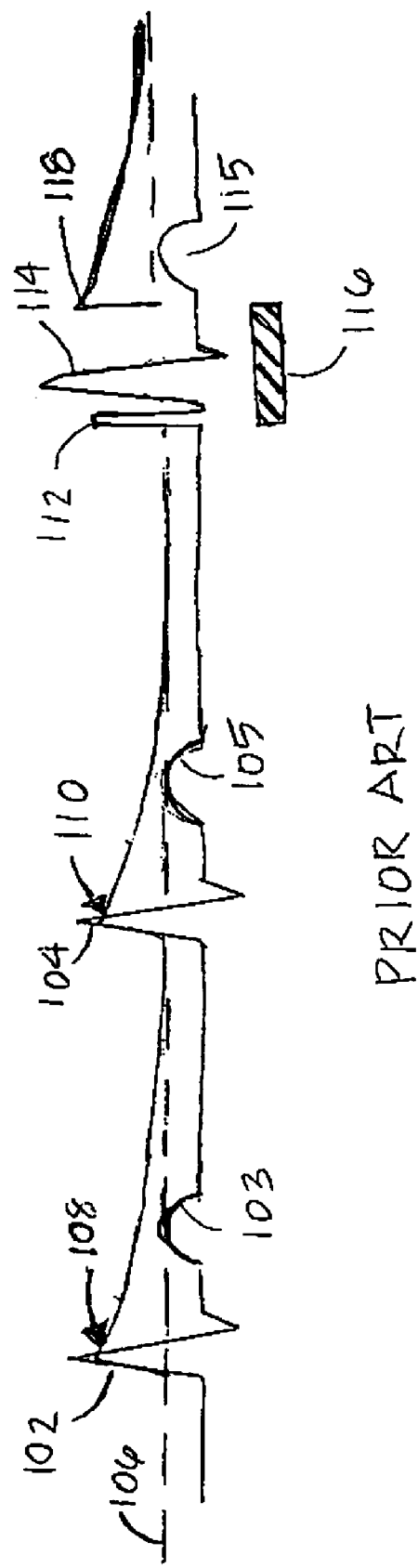
FIG. 4 (Prior Art) is a timing diagram illustrating known sensing operations associated with an exemplary EGM signal.

FIG. 4 is a timing diagram illustrating known sensing operations associated with an exemplary EGM signal. In FIG. 4, a sample EGM signal is shown including two intrinsic R-waves 102 and 104 each followed by T-waves 103 and 105, respectively. The EGM signal also includes a ventricular pacing pulse 112 followed by an evoked R-wave 114 and subsequent T-wave 115. Dashed line 106 represents the programmed ventricular sensing threshold. When R-waves 102 and 104 exceed the programmed sensing threshold 106, R-waves 102 and 104 are detected as ventricular sensed events, and the sensing threshold is adjusted to an increased value 108 and 110, respectively, which decays exponentially back to the programmed sensing threshold 106. The sensing threshold may be increased to a percentage of the sensed R-wave peak, up to some maximum multiple of the programmed sensing threshold. For example, the sensing threshold may be increased to 75% of the R-wave peak up to a maximum of 8 times the programmed sensing threshold 106. The automatically adjusted sensing threshold allows R-waves 102 and 104 to be sensed and prevents sensing of T-waves 103 and 105.

A pacing pulse 112 is delivered upon expiration of a ventricular pacing escape interval. According to prior art, a blanking interval 116 is initiated upon delivery of the pacing pulse 112 and extends beyong initiation of the pacing pulse 112 for a programmable period of time, for example on the order of 200 to 440 ms. At the end of the blanking period 116, the sensing threshold is automatically adjusted to a multiple of the programmed sensing threshold 106 at 118, e.g., 4.5 times the programmed sensing threshold, and exponentially decays thereafter to the programmed sensing threshold 106. The blanking interval 116, in addition to the automatically increased sensing threshold, reduces the ability to sense high rate intrinsic activity, particularly when the pacing rate is high.

During rate responsive pacing, the percentage of the cardiac cycle occupied by the blanking period 116 increases as the pacing rate increases. Typically, an upper pacing rate is specified to limit the maximum allowable pacing rate in order to prevent excessive "blinding" of the device to intrinsic activity. An upper pacing rate limit, also referred to herein as an "upper stimulation rate limit," may be set corresponding to an escape interval equal to twice the blanking interval or the longest arrhythmia detection interval to prevent pacing at rates within the arrhythmia detection zones.

Figure 5:
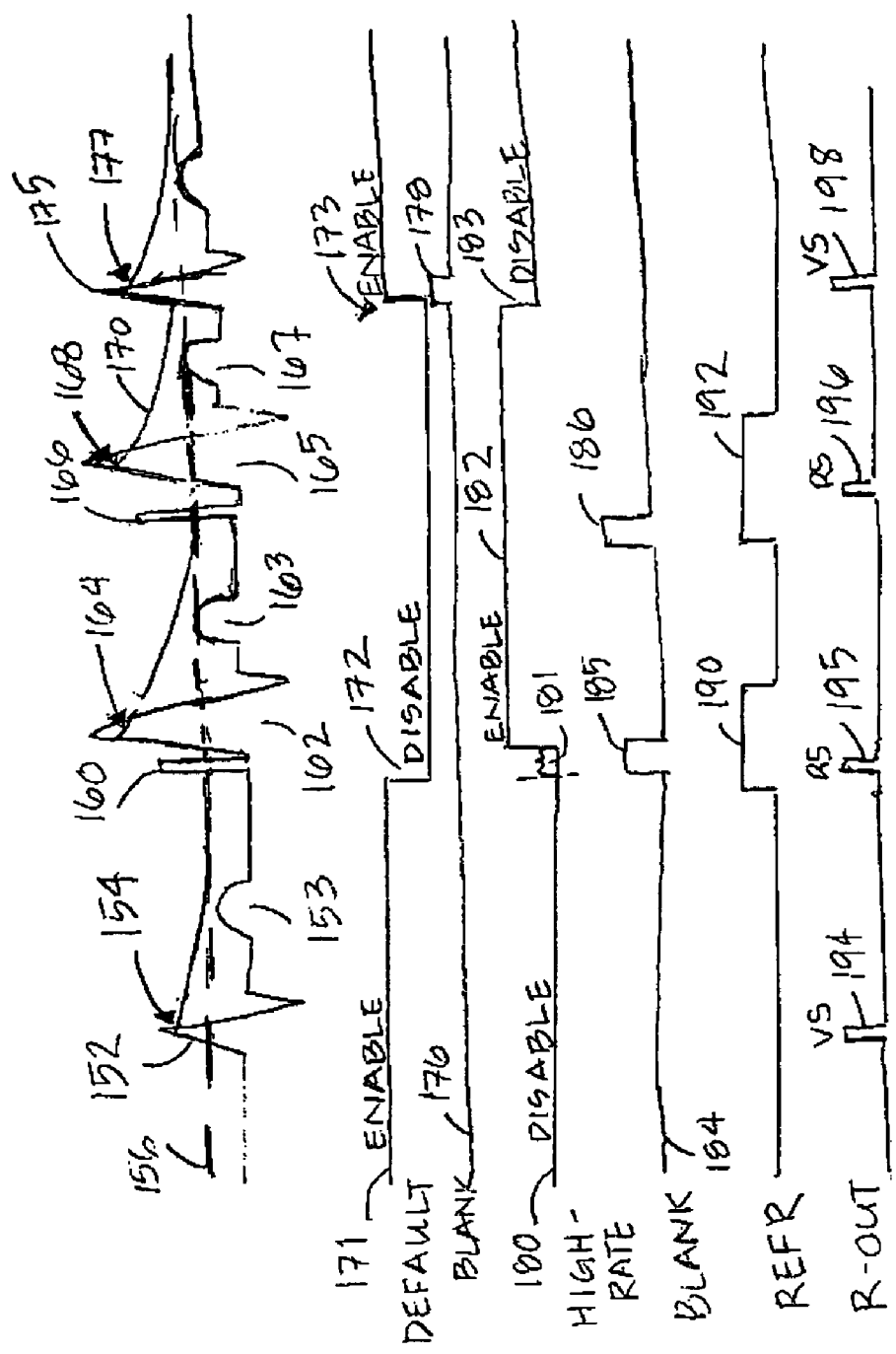
FIG. 5 is a timing diagram illustrating sensing operations according to one embodiment of the present invention.

FIG. 5 is a timing diagram illustrating sensing operations according to an embodiment of the present invention. A sample EGM signal includes an intrinsic R-wave 152 followed by a T-wave 153 and two pacing pulses 160 and 166 followed by evoked R-waves 162 and 165, respectively, and corresponding T-waves 163 and 167. The ventricular sensing threshold is adjusted automatically to a percentage of the intrinsic R-wave peak amplitude at 154 and decays exponentially thereafter to the programmed sensing threshold 156. Initially, default sensing is enabled at 171 for sensing intrinsic cardiac activity, and high rate sensing is disabled at 180. The intrinsic R-wave 152 is sensed by default sensing as a ventricular sense (VS) event 194 on the R-out signal line.

In this example, pacing pulses 160 and 166 are delivered at a high pacing rate, i.e., at a short escape interval, which is above a predetermined upper stimulation rate limit. As noted above, a predetermined upper stimulation rate limit may be defined based on a programmed blanking interval and/or arrhythmia detection intervals. When stimulation is initiated with pulse 160 above the predetermined upper rate limit, default sensing is disabled at 172, and high pacing rate sensing is enabled at 182. The sensing electrodes coupled to a sense amplifier may be automatically switched from a default sensing electrode configuration to a high pacing rate sensing electrode configuration that does not include the pacing electrode. Alternatively, a dedicated high pacing rate sense amplifier is enabled at 182, and a default sense amplifier is disabled at 172.

The high rate sensing may remain disabled for a short interval 181 during pacing pulse delivery and is then enabled in order to prevent sensing of pulse 160. Alternatively, the high pacing rate sensing configuration may be enabled immediately upon or just prior to pacing pulse delivery. Blanking intervals 185 and 186 may be applied to prevent sensing of the pacing pulses 160 and 166. In addition, blanking interval 185 may be applied to prevent sensing of a step voltage signal that might appear at the sense amplifier input upon switching sensing electrodes from a default configuration to a high pacing rate sensing configuration. The blanking intervals 185 and 186 are minimized, e.g. blanking intervals 185 and 186 may be on the order of 5 to 10 ms, because a post-pace polarization artifact will be minimal or absent at the high pacing rate sensing electrodes since these electrodes were not used in delivering a stimulation pulse.

Refractory periods 190 and 192 are initiated upon delivering pacing pulses 160 and 166, respectively, or alternatively at the end of blanking periods 185 and 186, respectively. Refractory periods 190 and 192 extend through a period of time following each pacing pulse 160 and 166 during which an evoked R-wave is expected to occur. Post-pace refractory periods 190 and 192 may be, for example, 120 ms to 250 ms in duration. The evoked R-waves 162 and 165 are sensed during the refractory period, as denoted by the refractory sense (RS) events 195 and 196 on R-OUT signal line. When sensed as refractory events, the evoked R-waves, do not reset the escape interval used for timing the delivery of the ventricular pacing pulses. These events are not counted as intrinsic cardiac events.

The ventricular sensing threshold may be automatically increased at 164 and 168 upon sensing the evoked R-waves 162 and 165, after which the sensing threshold decays to the programmed sensing threshold 156. The ventricular sensing threshold may be automatically adjusted, for example, to a multiple of the programmed sensing threshold, a percentage of the sensed evoked R-wave amplitude, a percentage of the previously sensed intrinsic R-wave amplitude using the default sensing electrode configuration, or a percentage of a previously sensed intrinsic R-wave using the high-rate sensing configuration. It is recognized, however, that automatic adjustments to the sensing threshold after switching to a high pacing rate sensing configuration is not necessary to practice the invention; a fixed sensing threshold may alternatively be applied during high rate pacing.

An intrinsic R-wave 175 is sensed as an intrinsic ventricular sense (VS) event 198 by the high pacing rate sensing configuration, prior to the expiration of the escape interval following pacing pulse 166. Detection of intrinsic activity during high rate stimulation will cause pacing to be withheld, as will be described further below, and the sensing electrode configuration to be switched back to the default sensing electrodes. Thus, high-rate sensing is disabled at 183 upon sensing event 198, and default sensing is enabled at 173. A short blanking interval 178 may be applied to the sense amplifier used for default sensing to prevent sensing of a step voltage signal that might appear at the input to the sense amplifier during electrode switching.

Figure 6:
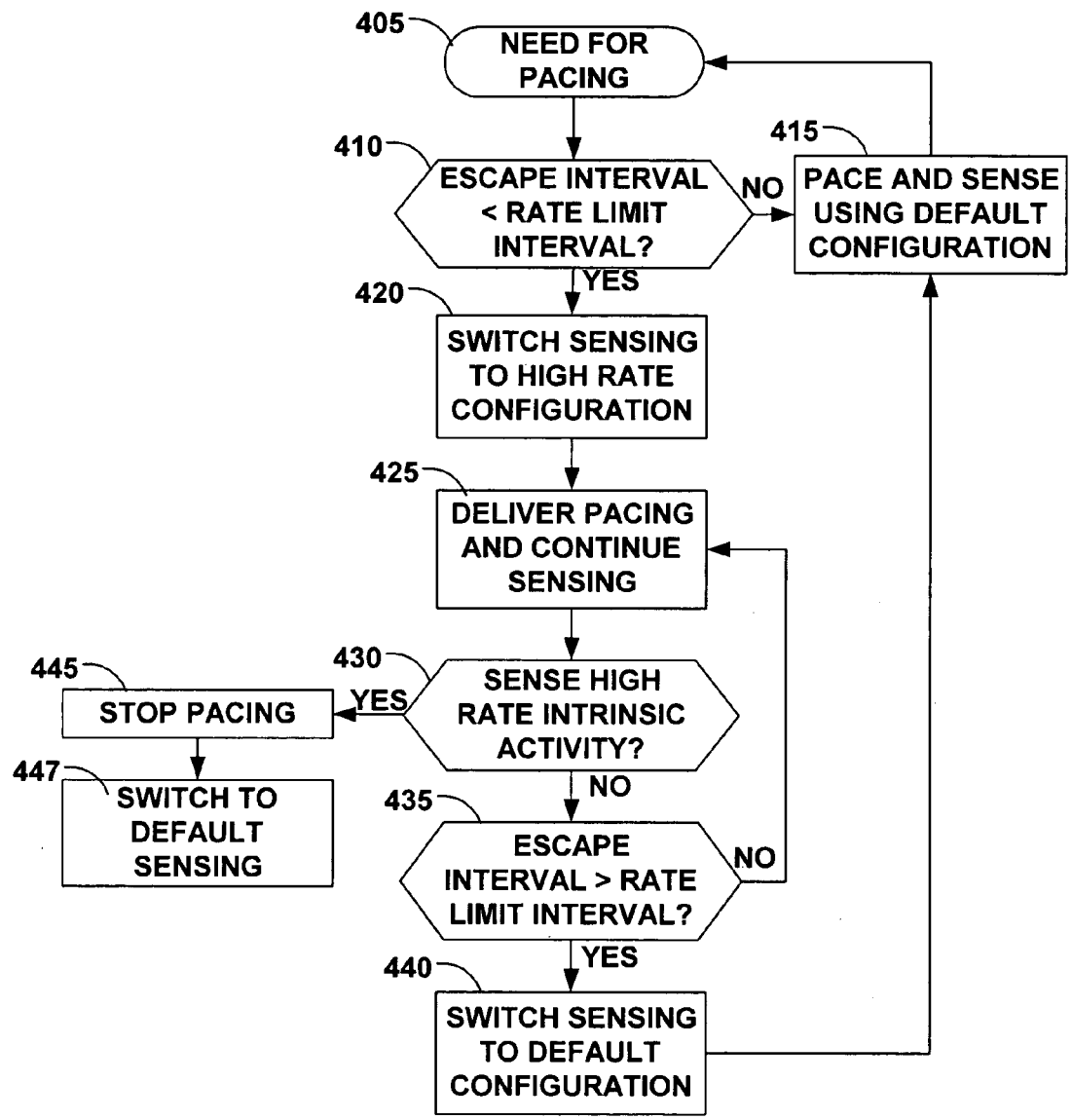
FIG. 6 is a flow chart summarizing the operation of a method for sensing intrinsic cardiac activity during high-rate pacing.

FIG. 6 is a flow chart summarizing the operation of a method for sensing intrinsic cardiac activity during high-rate pacing according to the present invention. The method shown in FIG. 6 is initiated upon detecting a need for pacing at step 405. In one application, the method of FIG. 6 is used during rate responsive pacing. A need for pacing may be determined at step 405 based on a mismatch in the current heart rate and the patient's metabolic need as determined from a physiological sensor. In other applications, other types of pacing therapies may be needed such as atrial overdrive pacing, extra systolic stimulation, atrial or ventricular rate stabilization pacing, or high rate pacing for preventing or suppressing arrhythmias.

At decision step 410, the escape interval used for timing the delivery of a stimulation pulse is compared to the interval corresponding to an upper pacing rate limit. An upper pacing rate is predefined, above which sensing using a default electrode configuration is considered unreliable in detecting high rate intrinsic activity due to sense amplifier blanking required to prevent sensing of the pacing pulse and ensuing afterpotential or polarization artifact. Automatic adjustments to the escape interval, for example during rate-responsive pacing or overdrive pacing, may result in an escape interval shorter than a rate limit interval. The rate limit interval may be a programmable setting or may be based on the currently programmed blanking interval and/or currently programmed arrhythmia detection intervals. For example, an interval limit for using a default sensing electrode configuration during pacing may be equal to the shorter of the longest programmed tachycardia detection interval or twice the blanking interval used during pacing.

If the escape interval remains longer than the rate limit interval, pacing and sensing are provided using default electrode configurations at step 415. For example, sensing may be provided using a conventional tip-to-ring bipolar sensing pair. The method of FIG. 6 continues to monitor the escape interval at step 410 as long as the need for pacing is sustained as identified at step 405.

If, however, the escape interval becomes shorter than the rate limit interval, the sensing electrode configuration is automatically switched to a high pacing rate sensing electrode configuration at step 420. As described above, the sensing electrode configuration may be switched using switching circuitry for changing the electrodes that are coupled to input lines of a sense amplifier or by disabling a default sense amplifier coupled to default sensing electrodes and enabling a dedicated high pacing rate sense amplifier coupled to high pacing rate sensing electrodes. At step 425, stimulation is delivered at the high rate corresponding to the shortened escape interval, and sensing for intrinsic activity continues during this high rate stimulation using the high rate sensing electrode configuration.

As indicated above, the high pacing rate sensing electrode configuration preferably eliminates the electrode pair used for pacing. In an embodiment that includes a tripolar lead having a tip, ring, and coil electrode, sensing during high rate stimulation is performed between the coil and device housing. Alternatively, sensing may be performed between the ring and coil. In an embodiment including a quadrapolar lead having a tip, ring and two coil electrodes, sensing during high rate stimulation may be performed between the two coil electrodes, or either coil electrode and the device housing, or the ring electrode and either coil electrode. The optimal sensing pair for reliably sensing of cardiac signals without interference from myopotential or other noise may depend on the lead placement and may vary between individuals.

Reliable sensing during high rate stimulation may also be achieved in embodiments that include an integrated bipolar lead. In one embodiment, stimulation and default sensing is performed between a tip electrode and a coil electrode and sensing during high rate pacing is performed using the coil electrode and device housing. In another embodiment, wherein an integrated bipolar lead includes two coil electrodes, such as a right ventricular integrated bipolar lead having a tip electrode, RV coil electrode, and SVC coil electrode, stimulation and default sensing may be performed between the tip electrode and a first coil electrode, e.g. the RV coil electrode, and sensing during high rate pacing is performed between the two coil electrodes, e.g. the RV coil and SVC coil, or alternatively between either coil electrode and the device housing.

With regard to the lead system shown in FIG. 1, a default atrial sensing electrode configuration may be the bipolar combination of tip electrode 17 and ring electrode 21, and the high pacing rate sensing electrode configuration may be SVC coil electrode 23 to housing 11. Likewise, a default ventricular sensing electrode configuration may be the bipolar combination of tip electrode 26 and ring electrode 24, and the high pacing rate sensing electrode configuration may be RV coil electrode 20 to housing 11. Alternatively, ventricular sensing during high rate ventricular pacing may be performed using CS coil electrode 8 and housing 11, or other sensing electrode(s) which may be available on a coronary sinus lead in combination with the CS coil electrode 8.

If intrinsic activity is sensed during the high rate pacing, as determined at decision step 430, pacing may be aborted at step 445 to allow the intrinsic rhythm to be evaluated for arrhythmia detection. The sensing configuration is preferably switched back to a default sensing configuration at step 447.

Thereafter, arrhythmia detection algorithms and therapies may be executed according to normal device operation. Any of the coil electrodes used for sensing during high rate stimulation are now available for connection to output circuitry if a cardioversion or defibrillation therapy is required.

Throughout high rate pacing, if no intrinsic activity is sensed as determined at decision step 430, the escape interval continues to be monitored at step 435. If the escape interval is lengthened again such that the escape interval is longer than the upper pacing rate limit interval, the sensing electrode configuration may be switched back to the default configuration, and pacing and sensing may continue at step 415. Thus the method shown in FIG. 6 provides a toggling of the sensing configuration between a high pacing rate sensing electrode configuration and a low or moderate pacing rate sensing electrode configuration such that pacing may be provided at relatively high rates with continued sensing of intrinsic cardiac activity.

It is recognized that the method shown in FIG. 6 may be applied during any cardiac stimulation therapy during which stimulation pulses are delivered at relatively high rates, i.e., at short escape intervals. Other cardiac stimulation therapies which may require delivery of pacing pulses at short escape intervals may include, but are not limited to, cardiac resynchronization therapy, extra systolic stimulation for achieving post-extra systolic potentiation, overdrive pacing for preventing or suppressing arrhythmias, stimulation for maintaining or restoring atrial or ventricular rate stability or treating cardiac-related breathing disorders, and anti-tachycardia pacing. During the delivery of any of these therapies, it may be desirable to sense intrinsic cardiac activity using an alternate, high pacing rate sensing electrode configuration when stimulation pulses are delivered at short intervals. Using a high pacing rate sensing electrode configuration, the required sense amplifier blanking may be limited to the time in which the stimulation pulse is delivered, thus minimizing the time in which the device is "blinded" to intrinsic cardiac activity.

Thus a method and apparatus that allow relatively uninterrupted sensing of intrinsic cardiac activity during high rate pacing is provided. High rate pacing may be delivered to meet the metabolic needs of the patient or treat a cardiac-related condition without limiting or impairing the detection of high rate arrhythmias. While the present invention has been described according to specific embodiments presented herein, these embodiments are intended to be exemplary, not limiting, with regard to the following claims.

I claim:

1. A medical device, comprising:
   a first plurality of electrodes forming a first electrode configuration to sense cardiac activity;
   a second plurality of electrodes forming a second electrode configuration to sense cardiac activity;
   a third plurality of electrodes to deliver a stimulation pulse in response to the sensed cardiac activity;
   a microprocessor determining whether an escape interval associated with the delivered stimulation pulse is less than a rate limit interval; and
   a control circuit switching from the first plurality of electrodes to the second plurality of electrodes in response to the escape interval being less than the rate limit interval.

2. The device of claim 1, wherein the rate limit interval corresponds to one of a blanking interval and an arrhythmia detection interval.

3. The device of claim 1, further comprising:
   an elongated lead body having a distal end;
   a first electrode positioned at the distal end of the lead body; and
   a second electrode positioned along the lead body proximal from the first electrode, wherein the first plurality of electrodes include the first electrode and the second electrode.

4. The device of claim 3, further comprising;
   a device housing housing the microprocessor and the control circuitry therein; and
   a coil electrode positioned along the lead body, wherein the second plurality of electrodes include the housing and the coil electrode.

5. The device of claim 3, further comprising a coil electrode positioned along the lead body, wherein the second plurality of electrodes include the second electrode and the coil electrode.

6. The device of claim 3, further comprising:
   a device housing housing the microprocessor and the control circuitry therein; and
   a first coil electrode and a second coil electrode positioned along the lead body, wherein the second plurality of electrodes include one of the first coil electrode and the second coil electrode, the first coil electrode and the device housing, the second coil electrode and the device housing, the first coil electrode and the second electrode, and the second coil electrode and the first electrode.

7. The device of claim 1, further comprising:
   an elongated lead body having a distal end;
   a first electrode positioned at the distal end of the lead body;
   a coil electrode positioned along the lead body proximal to the first electrode; and
   a device housing housing the microprocessor and the control circuitry therein, wherein the first plurality of electrodes include the first electrode and the coil electrode and the second plurality of electrodes include the coil electrode and the device housing.

8. The device of claim 1, further comprising:
   an elongated lead body having a distal end;
   a first electrode positioned at the distal end of the lead body;
   a first coil electrode and a second coil electrode positioned along the lead body proximal to the first electrode; and
   a device housing housing the microprocessor and the control circuitry therein, wherein the first plurality of electrodes include the first electrode and the first coil electrode and the second plurality of electrodes include one of the first coil electrode and the second coil electrode, the first coil electrode and the device housing, and the second coil electrode and the device housing.

9. The device of claim 1, wherein the control circuit switches from the second plurality of electrodes to the first plurality of electrodes in response to intrinsic cardiac activity being sensed via the second plurality of electrodes.

10. The device of claim 1, wherein the control circuit switches from the second plurality of electrodes to the first plurality of electrodes in response to the escape interval being greater than or equal to the rate limit interval.

* * * * *